(12) United States Patent
Klouzal et al.

(10) Patent No.: US 11,181,981 B2
(45) Date of Patent: Nov. 23, 2021

(54) METHOD AND APPARATUS FOR ENTRAINING SIGNALS

(71) Applicant: Interchange Laboratories, Inc., Chatsworth, CA (US)

(72) Inventors: Theodore J. Klouzal, Chatsworth, CA (US); Robert J. Plotke, Simi Valley, CA (US)

(73) Assignee: Interchange Laboratories, Inc., Chatsworth, CA (US)

( * ) Notice: Subject to any disclaimer, the term of this patent is extended or adjusted under 35 U.S.C. 154(b) by 765 days.

(21) Appl. No.: 15/993,348

(22) Filed: May 30, 2018

(65) Prior Publication Data
US 2018/0348864 A1 Dec. 6, 2018

Related U.S. Application Data

(60) Provisional application No. 62/512,671, filed on May 30, 2017.

(51) Int. Cl.
*G06F 3/01* (2006.01)
*G05B 15/02* (2006.01)
(Continued)

(52) U.S. Cl.
CPC ............ *G06F 3/015* (2013.01); *A61B 5/7225* (2013.01); *G02F 1/225* (2013.01); *G05B 15/02* (2013.01);
(Continued)

(58) Field of Classification Search
CPC ......... G06F 3/015; G02F 1/225; G05B 15/02; H03K 5/003; A61B 5/246; A61B 5/245;
(Continued)

(56) References Cited

U.S. PATENT DOCUMENTS 5,574,369 A 11/1996 Hibbs
5,724,188 A 3/1998 Kumagai et al.
(Continued)

FOREIGN PATENT DOCUMENTS

JP 7204352 8/1995
WO 00/03639 A1 1/2000
(Continued)

OTHER PUBLICATIONS

International Search Report and Written Opinion for International Application No. PCT/US2018/035184, Search completed Jul. 24, 2018, dated Aug. 9, 2018, 9 Pgs.
(Continued)

*Primary Examiner* — Gary Collins
(74) *Attorney, Agent, or Firm* — KPPB LLP

(57) ABSTRACT

Methods and apparatus configured to allow for users to intentionally interface with an external signal are provided. The methods and apparatus incorporate a randomly-generated electronic signal the behavior of which may be influenced to provide a control output. The methods and apparatus provide a temporal coherence measure influenced by a user that improves the ability to discriminate between intentionality and non-intentionality, and allow for the control of switching, communication, feedback and mechanical movement.

22 Claims, 8 Drawing Sheets

(51) Int. Cl.
| | |
|---|---|
| *H03K 5/003* | (2006.01) |
| *G02F 1/225* | (2006.01) |
| *A61B 5/00* | (2006.01) |
| *A61B 5/30* | (2021.01) |
| *A61B 5/245* | (2021.01) |
| *A61B 5/246* | (2021.01) |
| *A61B 5/291* | (2021.01) |

(52) U.S. Cl.
CPC .............. *H03K 5/003* (2013.01); *A61B 5/245* (2021.01); *A61B 5/246* (2021.01); *A61B 5/291* (2021.01); *A61B 5/30* (2021.01); *A61B 5/7257* (2013.01); *A61B 2560/0223* (2013.01); *A61B 2562/0214* (2013.01)

(58) Field of Classification Search
CPC ......... A61B 5/291; A61B 5/30; A61B 5/7257; A61B 2560/0223; A61B 2562/0214
See application file for complete search history.

(56) References Cited

U.S. PATENT DOCUMENTS

| | | | |
|---|---|---|---|
| 5,830,064 A | 11/1998 | Bradish et al. | |
| 6,008,642 A | 12/1999 | Bulsara et al. | |
| 6,024,700 A | 2/2000 | Nemirovski et al. | |
| 6,070,178 A * | 5/2000 | Anderson .............. | G06F 7/588 375/222 |
| 6,188,294 B1 * | 2/2001 | Ryan ..................... | H03B 29/00 327/164 |
| 6,249,009 B1 * | 6/2001 | Kim ....................... | G06F 7/588 250/580 |
| 6,324,558 B1 | 11/2001 | Wilber | |
| 6,762,605 B2 | 7/2004 | Brinker et al. | |
| 6,763,364 B1 | 7/2004 | Wilber | |
| 6,780,589 B1 | 8/2004 | Gulati | |
| RE44,097 E | 3/2013 | Wilber et al. | |
| 8,423,297 B2 | 4/2013 | Wilber | |
| 9,477,443 B1 * | 10/2016 | Belinski ................ | G06F 7/588 |
| 9,628,054 B1 | 4/2017 | Chen et al. | |
| 9,858,041 B2 | 1/2018 | Valentino et al. | |
| 2003/0219119 A1 * | 11/2003 | Kocarev ................ | G06F 7/588 380/28 |
| 2004/0139132 A1 * | 7/2004 | Lutkenhaus ........... | G06F 7/588 708/250 |
| 2007/0011217 A1 * | 1/2007 | Kim ....................... | G06F 7/588 708/250 |
| 2008/0183314 A1 | 7/2008 | Klouzal et al. | |
| 2010/0127756 A1 | 5/2010 | Balboni | |
| 2012/0294625 A1 | 11/2012 | Dynes et al. | |
| 2013/0036078 A9 | 2/2013 | Wilber | |
| 2014/0197865 A1 | 7/2014 | Feng et al. | |
| 2016/0117149 A1 * | 4/2016 | Caron .................... | G06F 7/588 708/255 |
| 2016/0328211 A1 * | 11/2016 | Nordholt ............... | G06F 7/588 |

FOREIGN PATENT DOCUMENTS

| | | |
|---|---|---|
| WO | 02/073386 A1 | 9/2002 |
| WO | 03/073175 A2 | 9/2003 |

OTHER PUBLICATIONS

Erol, "Quantum Entanglement: Fundamentals and Relations with Consciousness/Mind", NeuroQuantology, vol. 8, No. 3, Sep. 2010, pp. 390-402, DOI: 10.14704/nq.2010.8.3.309.
Fusaroli et al., "Timescales of Massive Human Entrainment", PLoS ONE, vol. 10, No. 4, Apr. 16, 2015, e0122742, 19 pages, https://doi.org/10.1371/journal.pone.0122742.
Gargiulo, "Mind, Meaning, and Quantum Physics: Models for Understanding the Dynamic Unconscious", The Psychoanalytic Review, Feb. 2010, vol. 97, No. 1, pp. 91-106, https://doi.org/10.1521/prev.2010.97.1.91.
Georgiev, "No-go Theorem for Stapp's Quantum Zeno Model of Mind-Brain Interaction", NeuroQuantology, vol. 13, Issue 2, Jun. 2015, pp. 179-189, DOI: 10.14704/nq.2015.13.2.839.
Gill, "Entrainment and musicality in the human system interface", AI & Society, Jun. 2007, vol. 21, Issue 4, pp. 567-605, DOI 10.1007/s00146-007-0103-8.
Gonze et al., "Stochastic models for circadian oscillations: Emergence of a biological rhythm", International Journal of Quantum Chemistry, vol. 98, Issue 2, Special Issue: Complexity: Microscopic and Macroscopic Aspects, 2004, pp. 228-238, first published Jan. 14, 2004, https://doi.org/10.1002/qua.10875.
Hari, "Mind and Tachyons: How Tachyon Changes Quantum Potential and Brain Creates Mind", NeuroQuantology, vol. 9, No. 2, Jun. 2011, pp. 255-270, DOI: 10.14704/nq.2011.9.2.320.
Hari, "Mind and Tachyons: Quantum Interactive Dualism—Libet's Causal Anomalies", NeuroQuantology, vol. 12, Issue 2, Jun. 2014, pp. 247-261, DOI: 10.14704/nq.2014.12.2.746.
Letiche, "Self-Organization, Action Theory, and Entrainment: Reflections inspired by Alicia Juarrero's Dynamics in Action", Emergence: Complexity and Organization, vol. 2, Issue 2, 2000, pp. 58-71, https://doi.org/10.1207/S15327000EM0202_04.
Liu et al., "Improvements and applications of entrainment control for nonlinear dynamical systems", Chaos, vol. 18, 2008, 043120, 23 pages, https://doi.org/10.1063/1.3029670.
Musha et al., "Possibility to Realize the Brain-Computer Interface from the Quantum Brain Model Based on Superluminal Particles", Journal of Quantum Information Science, vol. 1, No. 3, Dec. 2011, pp. 111-115, DOI: 10.4236/jqis.2011.13015.
Pantaleone, "Synchronization of metronomes", American Journal of Physics, vol. 70, No. 19, Oct. 2002, pp. 992-1000, https://doi.org/10.1119/1.1501118.
Shimizu et al., "Quantum Walk Founds Over Dispersion of Field RNG Output: Mind Over Matter Through Quantum Processes", NeuroQuantology, vol. 13, Issue 4, Dec. 2015, pp. 408-412, DOI: 10.14704/nq.2015.13.4.876.
Wolf, "Towards a Quantum Field Theory of Mind", NeuroQuantology, vol. 9, Issue 3, Sep. 2011, p. 442-458, DOI: 10.14704/nq.2011.9.3.456.
International Preliminary Report on Patentability for International Application PCT/US2018/035184, Report issued Dec. 3, 2019, dated Dec. 12, 2019, 08 Pgs.
Capra, F., "The Tao of Physics", 1975, pp. 68-69.
Chaneliere, T. et al., "Storage and retrieval of single photons transmitted between remote quantum memories", vol. 438(8), Dec. 2005, pp. 833-836.
Chapin et al., "Controlling robots with the mind", Scientific American-American Edition—287.4, Feb. 1, 2008, 14 pgs.
Chang, Y. F., "Experimental Tests of the Thought Field, The Extensive Quantum Theory and Quantum Teleportation", The Journal of Religion and Psychical Research, Oct. 2004, pp. 190-199.
Gammaitoni, L., "Nonlinear sensors activated by noise", vol. 325, Physica A: Statistical Mechanics and its Applications, Jul. 2003, pp. 152-164.
Jahn, R. G. et al., "On the Quantum Mechanics of Consciousness, with Application to Anomalous Phenomena", vol. 16(8), Foundations of Physics, 1986, pp. 721-772.
Kaku, M., "Parallel Worlds", 2005, 4 pgs.
Kal'yanov, E. V., "Interaction between Oscillations in a Self-stochastic System", vol. 45(10), Feb. 16, 2000, 1365-1367.
Libet, "Conscious Mind as a Field", Journal of Theoretical Biology, vol. 178, Issue 2, Jan. 21, 1996, pp. 223-224, https://doi.org/10.1006/jtbi.1996.0019.
McTaggart, "Sharing Dreams", 2002, 1 pg.
Mori, T. et al., "Stochastic Resonance in Alpha Oscillators in the Human Brain", vol. 12, International Journal of Bifurcation and Chaos (IJBC), 2002, 2631-2639.
Mould, R. A., "Quantum Brain States", vol. 33(4), Foundations of Physics, Apr. 2003, 591-612.
Mtetwa et al., "Precision Constrained Stochastic Resonance in a Feedforward Neural Network", IEEE Transactions on Neural Networks, Jan. 2005, vol. 16, No. 1, pp. 250-262.
Muratov, C. B. et al., "Self-induced stochastic resonance in excitable systems", vol. 210, 2005, 227-240.

(56) References Cited

OTHER PUBLICATIONS

Novin, W., "Can Quantum Physics Explain Consciousness?", vol. 11(1), 2004, 5 pgs.
Radin, D. I. et al., "Evidence of Consciousness-Related Anomalies in Random Physical Systems", vol. 19(12), Foundations of Physics, 1989, 1499-1514.
Rein, G., "Bioinformation Within the Biofield: Beyond Bioelectromagnetics", vol. 10(1), The Journal of Alternative and Complementary Medicine, 2004, 59-68.
Roy, P. K., "Stochastic Resonance Imaging—Stochastic Resonance Therapy: Preliminary Studies Considering Brain as Stochastic Processor", vol. 3316, Lecture Notes in Computer Science, 2004, 2 pgs.
Shermer, M., "Digits and Fidgets", vol. 288(1), Scientific American, Jan. 2003, 2 pgs.
Tiller, W. A. et al., "Can an Aspect of Consciousness be Imprinted into an Electronic Device?", vol. 35(2), Integrative Physiological and Behavioral Science, 2000, 142-163.

\* cited by examiner 1 of a multitude of capacitively-coupled signal sources

METHOD AND APPARATUS FOR ENTRAINING SIGNALS

CROSS REFERENCE TO RELATED APPLICATIONS

This application claims priority to U.S. Provisional Application Ser. No. 62/512,671, filed May 30, 2017, which is incorporated herein by reference in its entirety.

FIELD OF THE INVENTION

The current invention is directed to devices that detect the influence of external signals (e.g., mental intention changes) in the entrainment characteristics of a single signal source resulting from coupled multiple randomly-generated signals. The detected changes in coherence as measured by rate of change, and other electrical characteristics, are output as discrete measures of the entrained signals (e.g., mental intention), and systems are provided to control, for example, switching, communication, feedback, intention-influenced performance metric, and mechanical movement.

BACKGROUND OF THE INVENTION

Mind-machine interfaces seek to allow control of an object using thoughts and/or impulses stemming from thoughts. A number of research groups have disclosed methods and apparatus for detecting the influence of the mind on a physical construct. Some attempts to construct a mind-machine interface include using contacts placed on the head of an individual to detect changes in brain-impulse signals. In additional methods and apparatuses, the influence of the mind on a randomly-generated signal has been observed by processing a random digital number output by various methods. Examples of such methods and systems may be found, for example, in U.S. Patent Publication No. 2013/0036078; and U.S. Pat. Nos. 9,858,041; 8,423,297; RE44,097; U.S. Pat. Nos. 6,324,558; 6,763,364; and 6,762,605, the disclosures of each of which are incorporated herein by reference.

SUMMARY OF THE INVENTION

Many embodiments are directed to methods and apparatus configured to allow for very small amplitude signals such as those produced by human thought to influence the behavior of a randomly-generated electronic signal that can then be processed to provide a controlled output.

In various embodiments, the methods and apparatus describe an external intentionality interface apparatus, which includes a plurality of sub-atomic-based random signal sources, a coupling circuit in signal communication with the plurality of sub-atomic-based random signal sources, configured to combine the randomly-generated signals from the plurality of sub-atomic-based signal sources into a coupled randomly-generated signal capable of being entrained by an external intentionality signal, a signal amplifier in signal communication with the coupling circuit to amplify the coupled randomly-generated signal, a dynamic bias circuit to maintain a means-centered bias of the coupled randomly-generated signal, and a signal voltage trend indicator in signal communication with the signal amplifier and configured to detect the voltage difference between a non-delayed signal and a propagation-delayed signal, and to produce a trend output signal indicative of the voltage difference, where the digitally-processed trend output signal is provided at a first logic state where the trend is toward a negative voltage and a second logic state where the trend is toward a positive voltage, and wherein the trend output signal provides an indication of the presence of an external intentionality signal entrained within the coupled randomly-generated signal, each intention-entrained signal being a qualified event.

In a further embodiment of the methods and apparatus, the plurality of sub-atomic-based random signal sources comprise reverse-biased Zener diodes configured to produce multiple random signals at their respective breakdown voltage knees.

In another embodiment, of the methods and apparatus, the sub-atomic-based random signal sources comprise at least two Zener diodes.

In a still further embodiment of the methods and apparatus, the sub-atomic-based random signal sources comprise a laser photonic source.

In still another embodiment, the methods and apparatus include a photonic crystal waveguide interferometer configured to detect a greater phase state coherence and convert this phase state into a variable electrical signal.

In a yet further embodiment of the methods and apparatus, the plurality of randomly-generated signals are capacitively coupled.

In yet another embodiment of the methods and apparatus, the dynamic bias circuit is analog.

In a further embodiment of the methods and apparatus again, the output from the signal voltage trend indicator is a high or low logic state that is subsequently digitally processed using derivative calculations.

In another embodiment of the methods and apparatus again, the output signal from the signal voltage trend indicator is a high or low logic state that is output as a series of packets of discrete digitized frequency data, and the methods and apparatus further include a period-clock counting apparatus, where the period-clock counting apparatus normalizes the digitized frequency data as proportional values between adjacent digitized frequency values within each packet, generates a coherence score for the series of packets by summing the normalized digitized frequency data within each packet, determines the trend of the series of packets by determining changes in the coherence score between each packet in the series of packets, identifies frequency components of the trend by running FFT sampling for 10 seconds at 0.023 seconds per sample, sums the frequency components of the trend having a greatest percent difference between intention-entrained signals and signals that are not intention-entrained signals, and outputs the summed frequency components as a controlling signal.

In a further additional embodiment of the methods and apparatus, the presence of a qualified event in the digitally-processed trend output signal is utilized as a control signal for a device in signal communication therewith.

In another additional embodiment, the methods and apparatus further include a circuit feedback loop, where the circuit feedback loop is configured to determine at least one of the amount of qualified events and the temporal density of qualified events and automatically adjust the DC bias of the single randomly-generated signal generated from the coupled randomly-generated signals to set the central frequency of a set of higher and lower bandpass filters.

In a still yet further embodiment, the methods and apparatus include a plurality of nodes of multiple randomly-generated signals disposed in proximity to each other node and configured to entrain each other node such that the nodes act collectively to accomplish a programmed directive, via goal directed programming and feedback control processing of a set of filter module settings.

In still yet another embodiment, a method for entraining signals from a user in a randomly-generated signal to generate a control signal for controlling an external device includes providing an external intentionality interface apparatus to the user, and directing the user to make an intentional change to a state of an observable stimulus configured to be representative of the trend output signal.

In a still further embodiment again, a method for entraining signals from a user further includes processing the intentional change as a qualified event, and generating a control signal from the qualified event.

In still another embodiment again of the method for entraining signals from a user, the control signal directs the operation of an external device in signal communication with the mind-machine interface apparatus.

In a still further additional embodiment of the method for entraining signals from a user, the mind-machine interface apparatus further comprises an external device in signal communication with the mind-machine interface apparatus.

BRIEF DESCRIPTION OF THE DRAWINGS

The description will be more fully understood with reference to the following figures, which are presented as exemplary embodiments of the invention and should not be construed as a complete recitation of the scope of the invention, wherein.

DETAILED DESCRIPTION OF THE INVENTION

Figure 1:
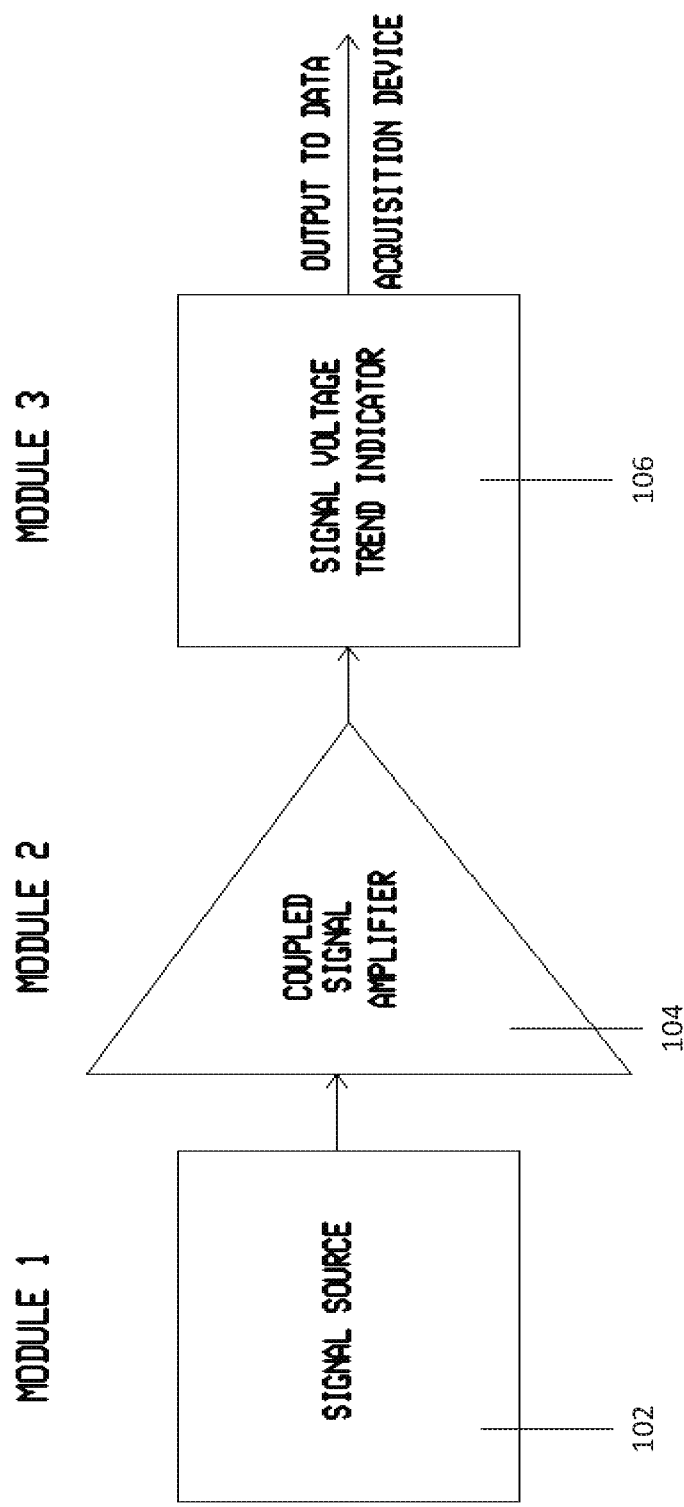
FIG. 1 provides a schematic diagram of a signal interface system in accordance with embodiments.

Turning now to the data and description, methods and apparatus configured to allow signals produced from mental thoughts to interface with a device generated signal are provided. In many such embodiments, the methods and apparatus incorporate a randomly-generated electronic signal the behavior of which may be influenced by an external signal to provide a control output. In various such embodiments, the methods and apparatus provide a temporal coherence measure influenced by an external signal (e.g., mental intention) that improves the ability to discriminate between an ambient state (e.g., where there is no external intentionality or mental signal) and an intentional state (e.g., where an eternal intentionality or mental signal is present). In some such embodiments, the methods and apparatus allow for the use of such of switching, communication, feedback, intention-influenced performance metric, and mechanical movement.

Embodiments of the invention allow for the integration and control of an external device to perform a designated task for which a user is required to respond. Embodiments allow for user influence and non-contact control of an external device determined by the sensitivity of the randomly-generated signals. In various embodiments, the sensitivity may be enhanced using a large plurality of randomly-generated signal sources. Embodiments allow for the output control of all forms of communication including self-feedback of all available organisms' perceptics. Embodiments allow for one or more users to influence the device to control external devices and feedback systems. Finally, some embodiments provide functionality whereby one device with two or more nodes of multiple randomly-generated signals in proximity to each other may entrain one another and via goal-directed programing and feedback control processing, act collectively to accomplish a programmed directive.

Entrainment is a natural phenomenon both in electronics, whereby two or more coupled asynchronous oscillating signals with differing periods and/or phases will tend to synchronize, and in biology, whereby two or more asynchronous biological organisms, systems or tissues with differing periods and/or phases will tend to synchronize similar biological characteristics. Biologic entrainment examples include the synchronization of the hand clapping of a crowd, of fireflies flashing, of consensus of thought, and of circadian rhythm. (See, e.g., Fusaroli, R., et. al., Timescales of Massive Human Entrainment, PLOS One, April 2015; Gill, S. P., Entrainment and Musicality in the Human System Interface, AI & Soc., 2007, 21, 567-605; Gonze, D., et. al., Stochastic Models of Circadian Oscillations: Emergence of a Biological Rhythm, International Journal of Quantum Chemistry, 2004, 98(2), 228-238; Letiche, H., Self-Organization, Action Theory, and Entrainment: Reflections Inspired by Alicia Juarreno's Dynamics in Action, Emergence: Complexity and Organization, April 2000, 58; Liu, F., et. al., Improvements and Applications of Entrainment Control for Nonlinear Dynamical Systems, Chaos, 2008, 18, 4, 43120; and Pantaleone, J., Synchronization of Metronomes, American Journal of Physics, 2002, 70, 10, 991-992, the disclosures of which are incorporated herein by reference.) This phenomenon has been known to drive a random system to a more coherent and synchronous state.

Some random generators, including the ones used in the present art, generate a random signal at the atomic or sub-atomic level. In turn, quantum theory provides the theoretical foundation and supports an explanation as to why a user (e.g., via mental intention) can, in theory, affect specific types of randomly-generated signals. (See, e.g., Erol, M., Quantum Entanglement, Fundamentals and Relations with Consciousness/Mind, NeuroQuantology, September 2010, 8(3), 390-402; Gargiulo, G., Mind, Meaning and Quantum Physics: Models for Understanding the Dynamic Unconscious, Psychoanalytic Review, February 2010, 97, 1, 91-106; and Har, S. D., Mind and Tachyons: How Tachyon Changes Quantum Potential and Brain Creates Mind, NeuroQuantology, June-11, 9, 2, 255-270, the disclosures of which are incorporated herein by reference.) Specifically, several researchers have established that the mind operates at a quantum level. (See, e.g., Wolf, F. A., Towards a Quantum Field Theory of Mind, NeuroQuantology, September 2011, 9, 3, 442-458; Georgiev, D., No-Go Theorem for Stapp's Quantum Zeno Model of Mind-Brain Interaction, NeuroQuantology, June-15, 13, 2, 179-189; Shimizu, T. & Ishikawa, M., Quantum Walk Founds Over Dispersion of Field RNG Output: Mind Over Matter Through Quantum Processes, NeuroQuantology, December 2015, 13, 4, 408-412; and Libet, B., Conscious Mind as a Field, Journal of Theoretical Biology, 1996, 178, 223-224, the disclosures of which are incorporated herein by reference.) Researchers have gone further to support the quantum-mind interaction by proposing that the mind generates a quantum field that can influence the quantum aspects of mechanical systems. (See, e.g., Hari. S. D., Mind and Tachyons: Quantum Interactive Dualism-Libet's Causal Anomalies, NeuroQuantology, June-14, 12, 2, 247-261; and Musha, T. & Sugiyama, T., Possibility to Realize the Brain-Computer Interface from the Quantum Brain Model Based On Superluminal Particles, Journal of Quantum Information Science, December 2011, 111-118, the disclosures of which are incorporated herein by reference.) Although there are opposing opinions as to whether the quantum interaction of an organism is generated from mind or the brain, the distinction is irrelevant to the operation of embodiments of the device that require only the generation of such interaction.

Embodiments of methods and apparatus provide an interface capable of entraining a user's intention (e.g., via mental signals) to influence randomly-generated signals such that they can be processed, discriminated and then output to fulfill the objective of user's intention. In many embodiments, methods and apparatus use multiple randomly-generated signals that, when coupled together, produce a higher state of synchronization (e.g., coherence) of the single random coupled signal. More specifically, the apparatus and methods utilize the entrainment of multiple randomly-generated signals, that when coupled together as a single random-generated signal, can manifest changes in entrainment characteristics when acted on by an external signal (e.g., a user's mental intention). This single random signal is then processed to detect the amount of synchronization (e.g., coherence) that is in a non-influenced (ambient) and influenced (intentional) state. Embodiments of the methods and apparatus also include a temporal processed measure of the coherence change in entrainment beyond an ambient state. Examples of measures of changes in entrainment coherence by a user include, but are not limited to, the control of switching, communication, feedback, and movement.

Embodiments of Interface Devices

Turning to the figures, as shown in FIG. 1, the methods and apparatus utilize a three module system. In a first "signal source" Module 1 (102), a plurality of random signals are generated and capacitively coupled together. These coupled signals from multiple sources are then amplified in a "coupled signal amplifier" in Module 2 (104). These random, coupled and amplified signals are then processed in Module 3 (106) by a signal voltage trend indicator that is configured to determine and output an indicator (e.g., high or low signal) indicative of the change in amplified signal voltage, and that when digitized and processed provides a measure of the level of synchronization or coherence in the signal, indicative of external influence. Details of each of these modules is provided below.

Figure 2:
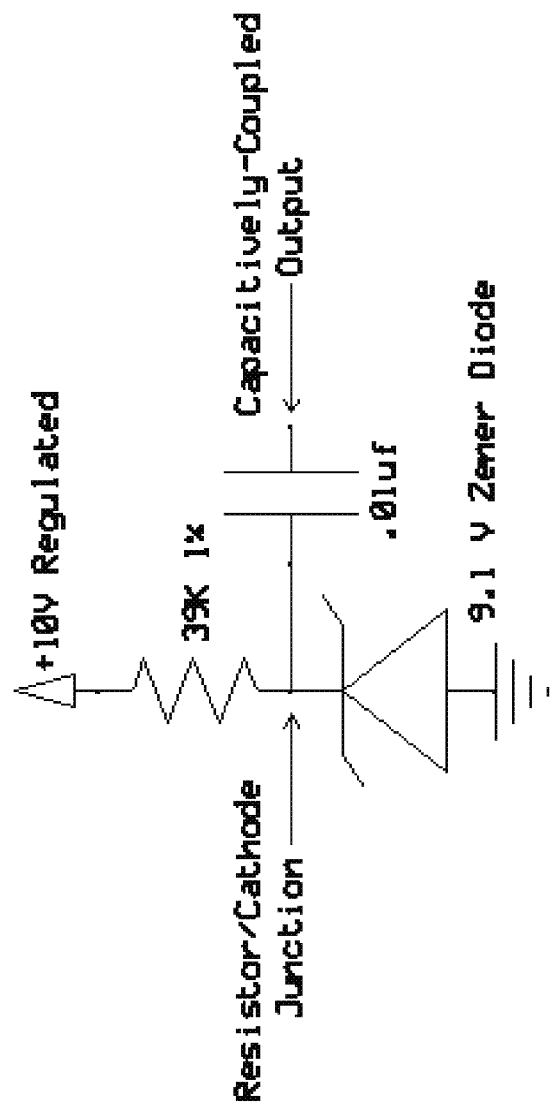
FIG. 2 provides a circuit diagram of a single randomly-generated signal source in accordance with embodiments.

In many embodiments, as shown in FIG. 1, Module 1 (102) uses two or more atomic or sub-atomic based random signal sources. In various embodiments, Module 1 (102) uses two or more reverse biased Zener diodes to produce multiple random signals at their respective breakdown voltage knees. It should be understood that any number or arrangement of such random signal sources may be used. In various embodiments, upwards of 40 such sources (e.g., Zener diodes) may be used to magnify the effect mind intention has as an entrained influence. In certain embodiments, upwards of 100 or upwards of 1,000 random signal sources may be used. Although any suitable Zener diode may be incorporated into the device in accordance with some embodiments (shown in FIG. 2), electrical random signals are produced by reverse biasing multiple Zener diodes, each through a 39K 1% resistor. In some embodiments, the diodes used are 9.1 Volt Zener diodes that operate within the avalanche breakdown region. In such embodiments, the combination of the Zener diode, resistor and coupling capacitor is considered the discrete "Signal Source" (see FIG. 1, item 102).

Although the above discussion has focused on diodes as the signal source, it will be understood that other methods and devices may be used to produce the two or more randomly-generated signals that can be coupled together and then converted to a form that is processed with present digital or proposed analog electronics. In various embodiments, a photonic method may be used to produce the two or more randomly-generated signals by manipulation and processing of laser photons. In other embodiments, a photonic crystal waveguide interferometer in the combined multiple laser signals may be used to detect a greater phase state coherence. In such embodiments a photo detector may be used to convert this phase state into a variable electrical signal that, when processed to detect changes in coherence or other signal characteristics, is used as a controlling source.

Figure 3:
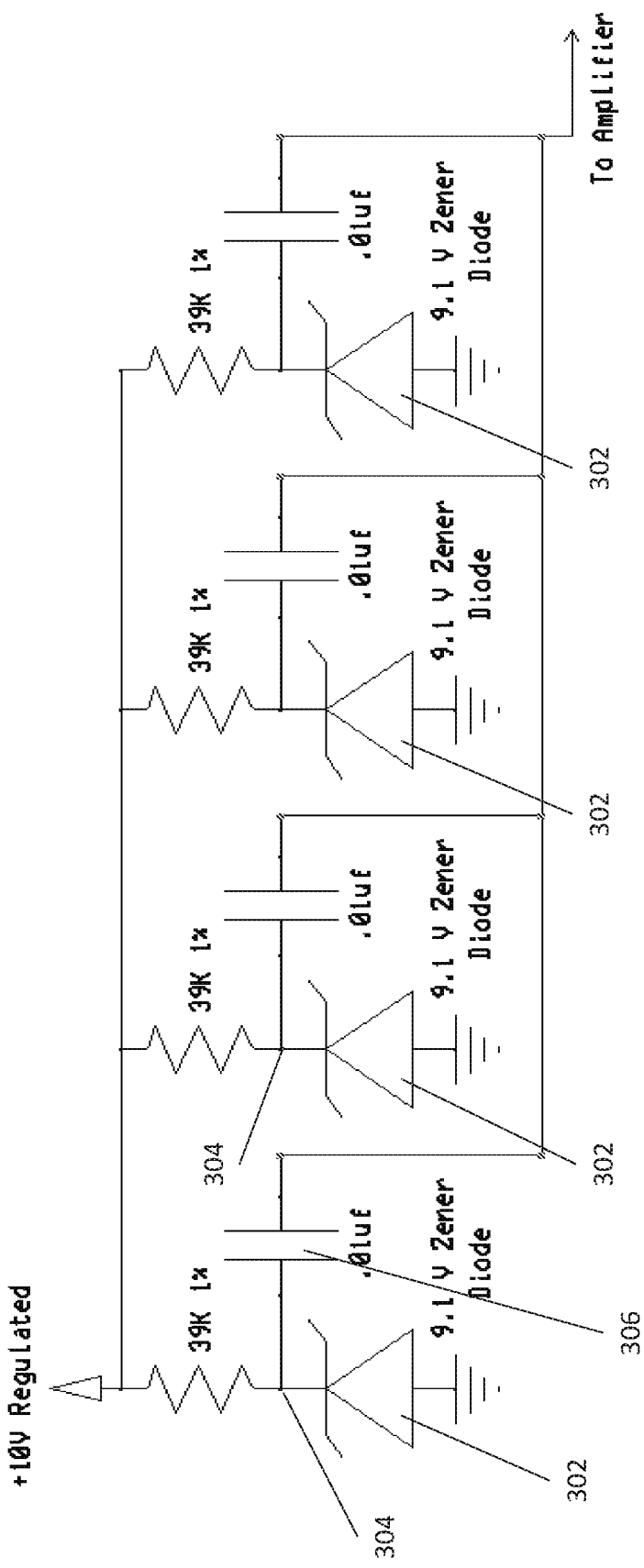
FIG. 3 provides a circuit diagram of a plurality of randomly-generated signal sources capacitively coupled together in accordance with embodiments.

In various embodiments, the individual signals from the randomly-generate signals from the individual sources are capacitively coupled to combine the plurality randomly-generated signals. One exemplary coupling mechanism in accordance with embodiments is shown in FIG. 3. As shown, in many embodiments (e.g., where a diode (302) is used to produce the randomly-generated signals) the signals are coupled at the resistor/Zener cathode junction (304) through a 0.01 uf ceramic capacitor (306) to produce a signal with no DC bias, (see, FIG. 3). In one exemplary embodiment, forty individual signal sources are capacitively coupled to produce a single Signal Source output to Module 2 (see, FIG. 1, item 104).

Regardless of the specific mechanism used in the Signal Source, the output of the Signal Source is taken and coupled to combine the signals from the individual sources. The coupling of random signal sources produces an entrained signal which by its nature has a coherence that can be measured. According to embodiments this entrained signal may be influenced at the source level prior to coupling, while coupling allows the device to acquire a measure of sensitivity to entrainment, and by entraining multiple signal sources the organizational effect of an external influence on the random signal sources may be magnified.

Figure 4:
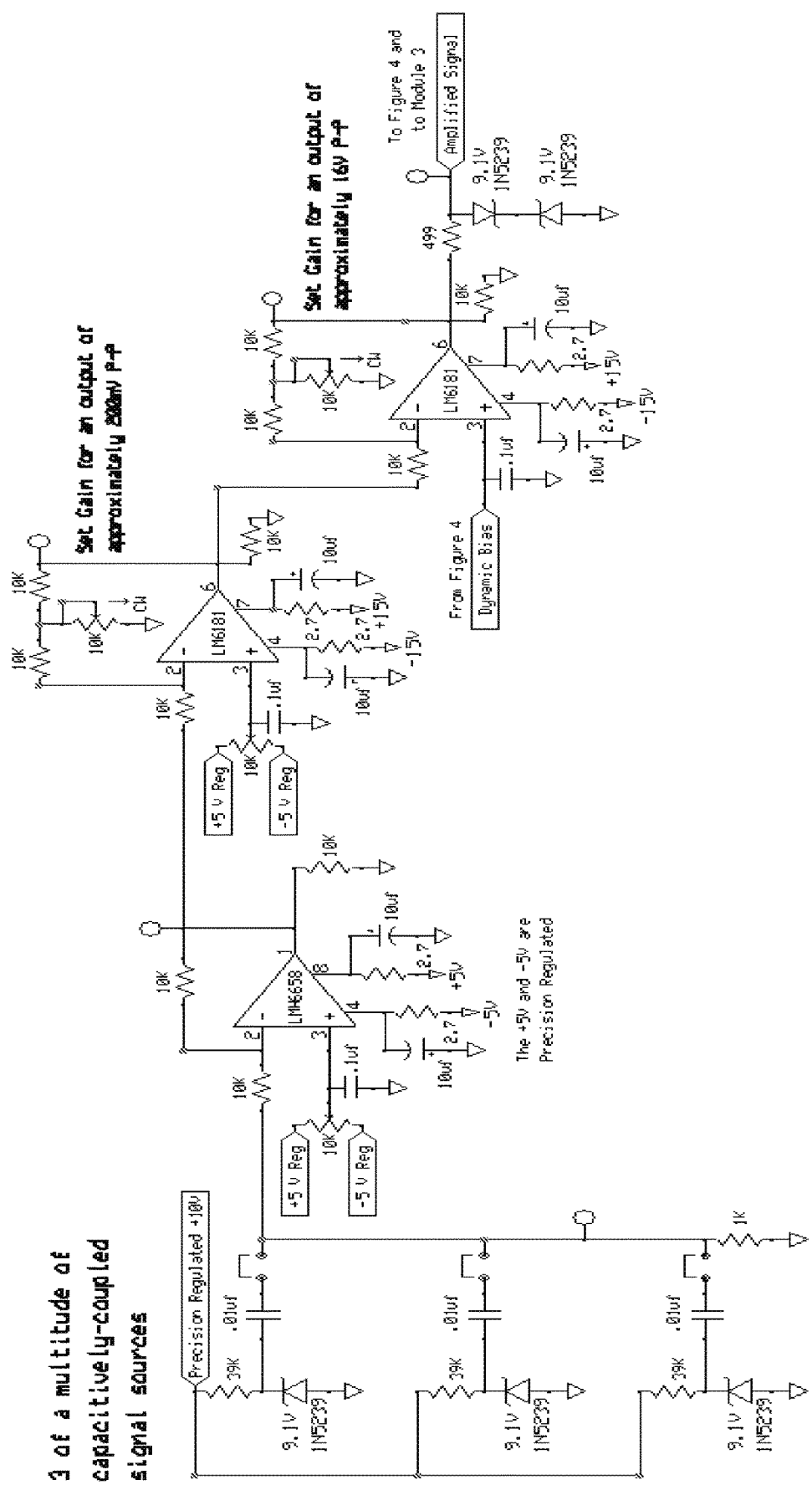
FIG. 4 provides a circuit diagram of a signal amplifier in accordance with embodiments.
Figure 5:
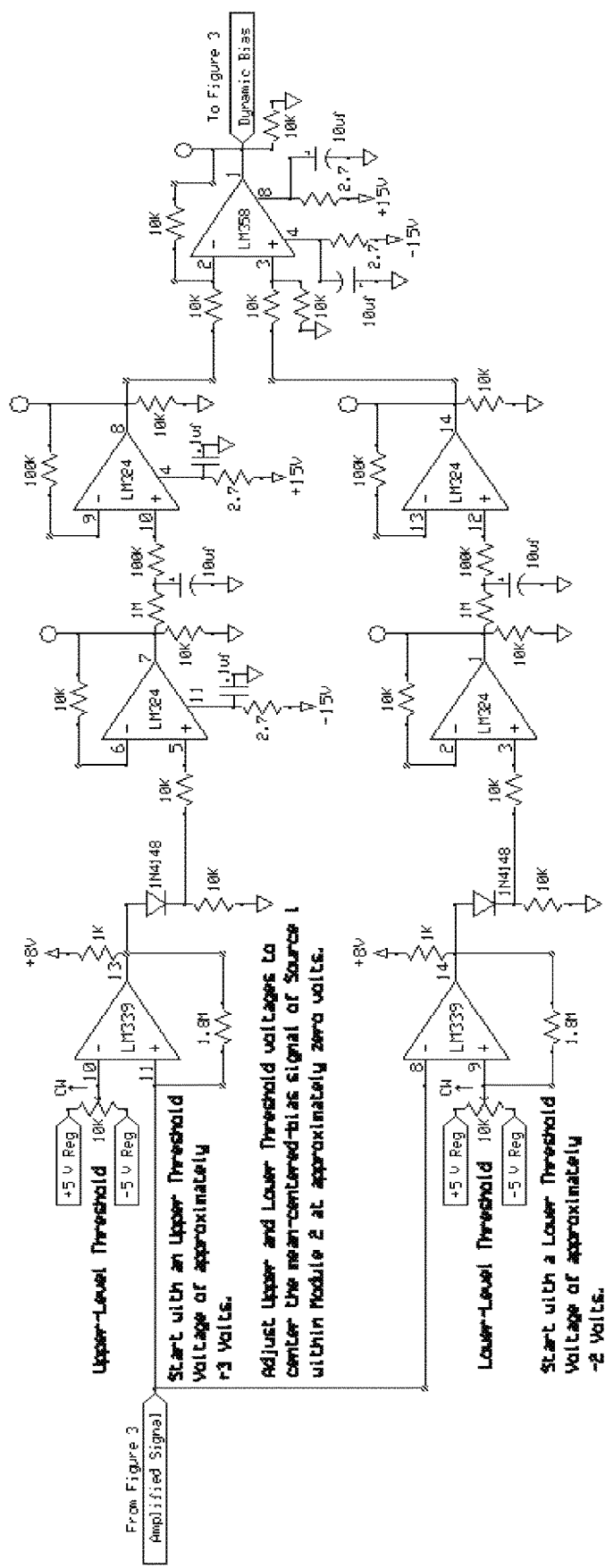
FIG. 5 provides a circuit diagram of a dynamic bias circuit in accordance with embodiments.

As shown in FIG. 1, the coupled randomly-generated signals are then amplified in Module 2 (104). As shown in FIG. 4, Module 2 amplifies the capacitively-coupled signals from multiple signal sources. In various embodiments, Module 2 is also configured to automatically maintain a mean-centered bias to correct for thermal drift. In some such embodiments, Module 2 is provided a dynamic bias circuit (as shown in one exemplary embodiment in FIG. 5) to prevent drift and further regulate the amplified signal. In many embodiments, the output of Module 2 is a 10 volt peak-to-peak signal that is then transmitted for processing by Module 3.

Figure 6:
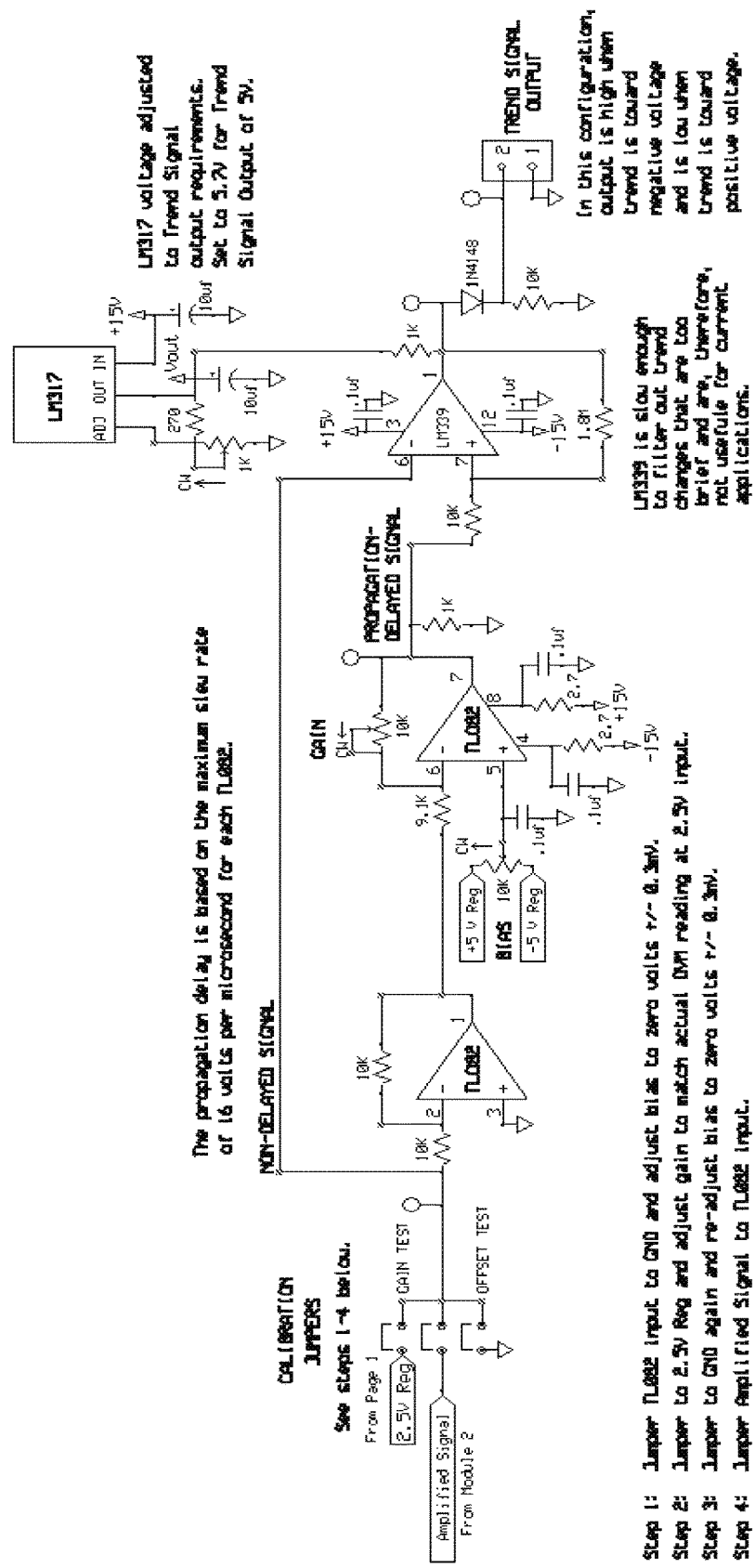
FIG. 6 provides a circuit diagram of a signal trend indicator in accordance with embodiments.

In many embodiments of Module 3, the capacitively-coupled and amplified signal is processed by a Signal Voltage Trend Indicator configured to output a logic state (e.g., high or low) indicative of the signal voltage trend indicator circuit. This logic state is then sent to data acquisition hardware for period-clock counting and output of discrete digitized frequency data. As shown in FIG. 6, in various embodiments, Module 3 may be configured to use a comparator (e.g., an LM339 comparator) to detect the voltage difference between a non-delayed signal and a propagation-delayed signal. In some such embodiments, the propagation delay is based on the maximum slew rate of 16 volts per microsecond for each operational amplifier (e.g., TL082 amplifier) shown in FIG. 6. The configuration shown in FIG. 6 is designed such that the output of the comparator is high when the trend is toward negative voltage and low when the trend is toward positive voltage.

It should be understood from the exemplary circuit of FIG. 6 that the Trend Signal Output may be adjusted to any voltage for any digital acquisition format. In one exemplary embodiment, when the amplified signal voltage is trending negative, the Trend Signal Output is in a High logic state, and when the amplified signal voltage is trending positive, the Trend Signal Output is in a Low logic state. In various embodiments, the logic state output may be designed for digital acquisition and signal processing.

In some embodiments of the exemplary circuit in FIG. 6 a method to have multiple voltage-controlled trend signal outputs (nodes) of various frequency bands. In various embodiments, the logic state output may be designed for digital acquisition and signal processing.

In some embodiments of multiple frequency trend signal output nodes, the nodes are in various ways weighted, valuated, and/or combined to produce a controlling output.

In some embodiments the multiple frequency trend output nodes are controlled by a feedback loop that changes one or various voltages to alter the timing of the trend signal circuits (FIG. 6) to change the one or various multiple frequency trend signal nodes controlling output.

In some embodiments multiple frequency trend signal output nodes are compared to a single or a bandpass of frequencies using the trending as a phase synchronizing frequency coherence comparator.

In some embodiments, the Signal Voltage Trend Indicator may output packets of discrete frequency values to processing software in a period clock-counting apparatus. In various embodiments, an output packet may contain 1,000, 5,000, 10,000, 50,000, 100,000, or more frequency values. The frequency values are normalized as proportional values of one frequency value to its adjacent value the output packet. In certain embodiments, these proportional values are summed up to the total number of discrete frequency values to generate a coherence score for an output packet. As a non-limiting example, coherence can be discriminated considering that 100% coherence of two adjacent frequency values would equal 1; therefore, 100% coherence of each of 1,000 frequency values is equal to a coherence score 1,000 for the output packet. Some embodiments determine a trend in coherence by identifying change in the coherence score between output packets. In some embodiments, the average trend may be output as a controlling signal.

In accordance with embodiments, a circuit feedback loop may be provided that, in response to the amount and/or the temporal density of qualified events, automatically adjusts the DC bias of the single randomly-generated signal generated from the coupled randomly-generated signals to set the central frequency of a set of higher and lower bandpass filters. A quality metric may be constructed by filtering low frequency trends, which are associated with functional movement patterning, which is approximately 0.25 Hz. In some embodiments, timing components of each wave form may be compared to the next wave form to calculate the proportional relationship. A derivative bias for each wave form and quality metric can be derived from the division of the derivative bias into the time proportionality. A greater quality metric value is thus associated with a proportionality of 100% (or 1) and a derivative bias that is closer to 0. In various embodiments, frequency components of signal trends may be detected using fast Fourier transform (FFT). In various embodiments, FFT sampling may be run for an amount of time to identify relevant frequency changes in the trend. In some embodiments, the relevant frequency changes are fast changes, and the FFT sampling may be run for times of 1 second, 2 seconds, 3 seconds, 4 seconds, or 5 seconds. In certain embodiments, the relevant frequency changes may be slow changes, where longer sampling times may be used, such that FFT sampling may be run for 10 seconds, 15 seconds, 30 seconds, 1 minute, 5 minutes, or a longer time.

Further, some embodiment may perform FFT sampling may be run at sampling rates to capture frequency values as these samples are generated. For example, if 1000 frequency values are generated every 23 seconds, an FFT sampling may be run at approximately 0.023 seconds/sample. In certain embodiments, the frequency values may be generated at a faster or slower rate, such that FFT sampling may be run at a rates of approximately 0.005 seconds/sample, approximately 0.01 seconds/sample, approximately 0.015 seconds/sample, approximately 0.02 seconds/sample, approximately 0.025 seconds/sample, approximately 0.03 seconds/sample, approximately 0.035 seconds/sample, approximately 0.04 seconds/sample, approximately 0.045 seconds/sample, approximately 0.05 seconds/sample, or greater. By detecting signal trends, various embodiments can suppress effects of an external influence by accessing specific frequencies, when in an ambient state. Thus, in various systems in accordance with embodiments, feedback control is now possible, because these systems can access specific frequencies, which are more prominent with a specific external influence source associated with the rise and fall signal trends.

Utilizing the interface device and method described above, it is possible to use the control functionality for a variety of purposes including, but not limited to: an on and off switch activated when a predetermined threshold of coherence per unit time has been reached, an array control system that utilizing the slope direction per unit time of qualified instances of entrainment coherence influenced by mental intention, and an informational coding of the processed signal that is determined to be a unique characteristic of the effect on intention only. In some embodiments, an interface apparatus may use one or more of these listed uses to control a device in communication with the interface, such that the apparatus may turn on or off a lightbulb, open and close mechanical devices, such as a robotic hand, or any other mechanical, physical, or computational process.

Embodiments of Methods of Entraining

Figure 7:
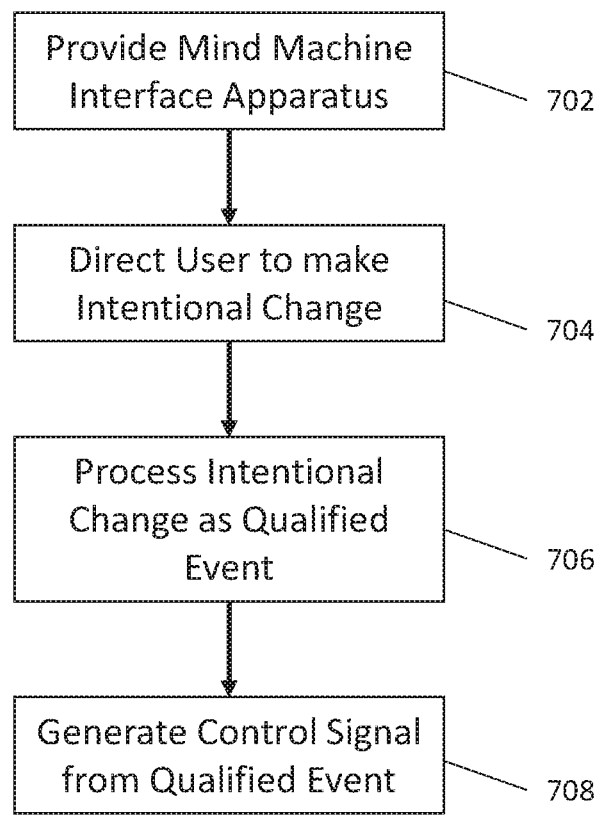
FIG. 7 provides a flow diagram of a method of entraining intentional signals in a randomly-generated signal in accordance with embodiments.

Turning now to FIG. 7, some embodiments include a method (700) to entrain an external influence (e.g., a user's thoughts) using a device or apparatus as described above. In such embodiments, an interface apparatus as described above may be provided to a user (702). The user may further be directed to (704) to make an intentional change to a state of an observable stimulus configured to be representative of the trend output signal in embodiments of an interface apparatus as described above. In additional embodiments, this intentional change may further be processed (706) as a qualified event as described above. And, methods of some embodiments may further generate (708) a control signal from the qualified event. Such control signals may be used by some embodiments to control an external device which is in signal communication with the interface apparatus.

Figure 8A:
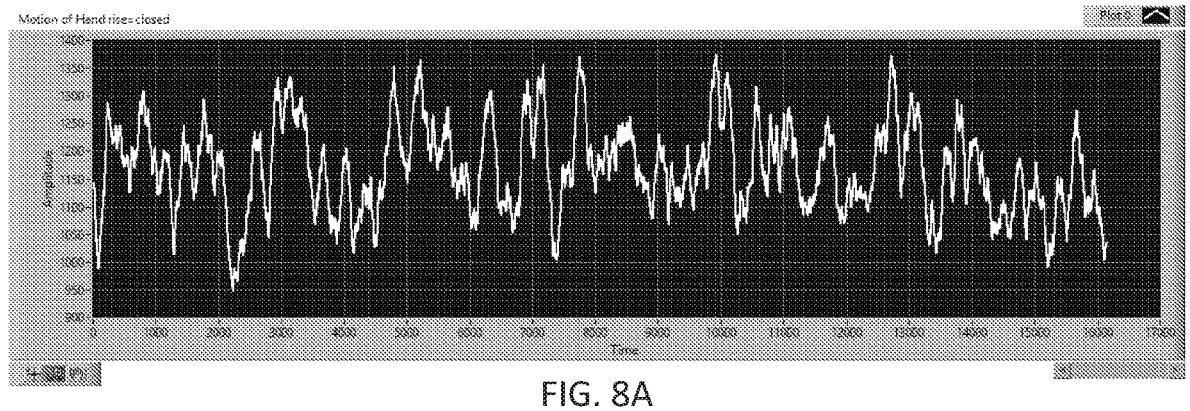
FIG. 8A illustrates a non-intentional wave form pattern in accordance with embodiments.
Figure 8B:
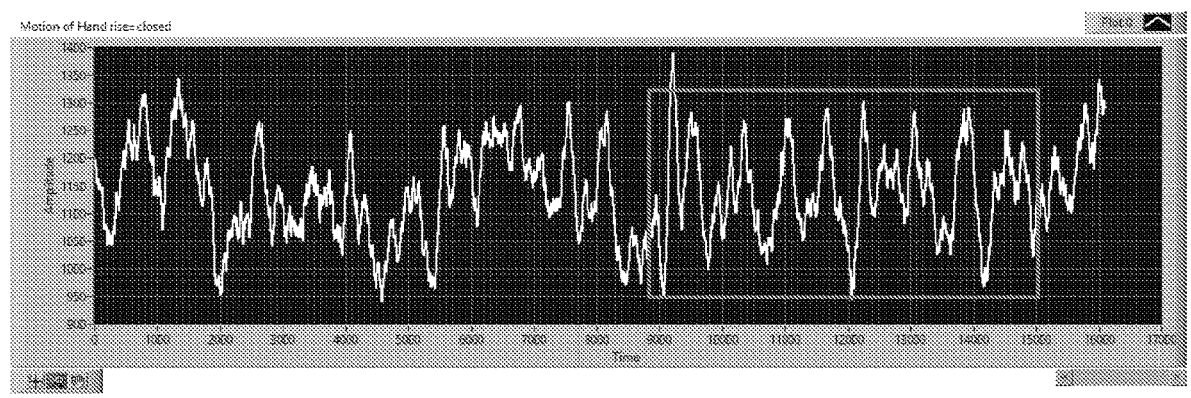
FIG. 8B demonstrates an intentional signal wave form pattern in accordance with embodiments.

Turning now to FIGS. 8A and 8B, entrainment of signals can be seen by how wave forms are formed in accordance with some embodiments. FIG. 8A illustrates a wave form generated by a non-intention trial, where the plurality of randomly-generated signals are plotted over time in accordance with various embodiments. In FIG. 8B, a wave form is plotted for an intention trial in accordance with some embodiments. The box running from approximately 9,000 to approximately 15,000 highlights an area where mental intention has begun to entrain the randomly-generated signals in accordance with certain embodiments. In this highlighted area, the wave form has a greater uniformity in coherent wave pattern as a user intends to affect a change in a device. It should be noted that the intentional change may include numerous types of devices, including physical devices or computational devices. Physical devices are such devices that have a physical effect, such as opening and closing a mechanical hand or turning on and off a light bulb, whereas computational devices may have an effect on a computer or other device, such that the intentional change may affect input into the device, such as typing or moving a cursor.

Exemplary Embodiments

Although certain exemplary embodiments of the operation of an interface apparatus are provided below, it should be understood that these examples are illustrative in nature, and are not intended to be limiting as to the scope of the current disclosure.

Example 1: Study of Device Sensitivity to Entrainment

Methodology: In one exemplary study, thirty-four (34) adult subjects participated in a research project using a device as described in reference to FIGS. 1-6. Prior to participation, a trial was performed in an empty room. A 5-minute delay in data capture was set, and then 5 minutes of unprocessed frequency data was digitally saved. Each participant performed three 5-minute trials where he/she was requested to change the characteristics of a moving tracing on a computer screen. The moving tracing represented the amount of coherence associated with the device's signal output.

Data analysis: The unprocessed frequency data was processed from frequency to the time period in milliseconds. This transformation was used to obtain the number of frequency values required to obtain a period from 10 milliseconds to 200 milliseconds in 10 millisecond increments (300 seconds where parsed using each time frame resulting in an N values between N=30,000 to and N=5). These periods where used to parse the frequency data to calculate the following:

The $2^{nd}$ derivative of each period from 10 milliseconds to 200 milliseconds in 10 millisecond-increments. Histogram sorting separated derivative values into 10 discrete bins.

The bias of the $2^{nd}$ derivative separated into three histogram bins. The range of the derivative bias was calculated to determine the percent of values allocated to each of three bins. The lowest histogram bin contains 36%, the central histogram bin contains 28%, and the highest histogram bin contains 36% of the values. This provided the greatest mean discrimination between the three bins.

The running statistical mode's frequency was within a 7000 Hz bandwidth.

The mean of each processed value for each time frame was calculated.

Processing of the $2^{nd}$ derivative, the derivative bias and the statistical mode's frequency produced 2700 values each; from 34 participants with 4 trials each (one non-intend and 3 intention trials), and 20 discrete analysis time frames from 10 to 200 milliseconds in 10 millisecond increments. A statistical ANOVA (Analysis of Variance) was performed on the three processed types comparing Trial 0, the non-intention (empty room) trial with the three intend participant trials, (trials 1, 2 and 3). The data from these trials is provided in Tables 1-15, below. (Note for all tables a mean difference is significant at the 0.05 level.)

Results: There was a statistically significant difference in the $2^{nd}$ derivative processing at a p=0.000 between the non-intend trial 0 and each of intend trials 1, 2 and 3. There was no statistically significant difference at a p>0.05 between the intention trials 1 to 2, 1 to 3 and 2 to 3. There was a statistically significant difference in the 2nd derivative bias processing at a p=0.013 between the non-intend trial 0 and trial 1, and a p=0.000 between the non-intend trial 0 and intend trials 2 and 3. There was a statistically significant difference in the statistical mode's frequency processing at a p=0.036 between the non-intend trial 0 and trial 1, p=0.015 between the non-intend trial 0 and intend trial 2 and a p=0.030 between the non-intend trial 0 and intend trial 3.

Accordingly, there is a statistical difference between trials with users versus those control trials, both in the derivative, derivative bias and frequency shift of the statistical mode of the raw frequency data. The statistical results support that embodiments of the interface apparatus can produce a randomly-generated signal and detect an external influence on that signal by a user. This study supports the foundational theory that users actively entrain a device that is already sensitive to entrainment influence. It is apparent from the derivative statistical evidence that users organize a random signal by increasing its coherence; creating greater consistency in the signal's rate of change. It is further apparent that users are able to create a frequency shift when influencing a random signal. Accordingly, these results indicate that there is strong statistical evidence that user intention affects the present device using its entrained signal and rate of change and frequency shift processing.

TABLE 1

Results from Statistical ANOVA for Derivative Mean Values

| Dependent Variable | (I) Trial Number | (J) Trial Number | Mean Difference (I − J) | Std. Error | Sig. | 95% Confidence Interval Lower Bound | 95% Confidence Interval Upper Bound |
|---|---|---|---|---|---|---|---|
| Bin 1 | 0 | 1 | .1498937828326* | .0303513558274 | .000 | .069745632142 | .230041933523 |
|  |  | 2 | .1298707827505* | .0303371893106 | .000 | .049760041266 | .209981524235 |
|  |  | 3 | .1546338322999* | .0305694581779 | .000 | .073909743581 | .235357921019 |
|  | 1 | 0 | −.1498937828326* | .0303513558274 | .000 | −.230041933523 | −.069745632142 |
|  |  | 2 | −.0200230000821 | .0305702982435 | 1.000 | −.100749307144 | .060703306980 |
|  |  | 3 | .0047400494673 | .0308008092868 | 1.000 | −.076594962983 | .086075061917 |
|  | 2 | 0 | −.1298707827505* | .0303371893106 | .000 | −.209981524235 | −.049760041266 |
|  |  | 1 | .0200230000821 | .0305702982435 | 1.000 | −.060703306980 | .100749307144 |
|  |  | 3 | .0247630495494 | .0307868495859 | 1.000 | −.056535099829 | .106061198928 |
|  | 3 | 0 | −.1546338322999* | .0305694581779 | .000 | −.235357921019 | −.073909743581 |
|  |  | 1 | −.0047400494673 | .0308008092868 | 1.000 | −.086075061917 | .076594962983 |
|  |  | 2 | −.0247630495494 | .0307868495859 | 1.000 | −.106061198928 | .056535099829 |

*The mean difference is significant at the 0.05 level.

TABLE 2

Derivative Bias Analysis

|  | Cases Included N | Cases Included Percent | Cases Excluded N | Cases Excluded Percent | Cases Total N | Cases Total Percent |
|---|---|---|---|---|---|---|
| Mean High * Trial Number | 2700 | 100.0% | 0 | 0.0% | 2700 | 100.0% |
| Sum High * Trial Number | 2700 | 100.0% | 0 | 0.0% | 2700 | 100.0% |
| Percent High * Trial Number | 2700 | 100.0% | 0 | 0.0% | 2700 | 100.0% |
| Mean Central * Trial Number | 2700 | 100.0% | 0 | 0.0% | 2700 | 100.0% |
| Sum Central * Trial Number | 2700 | 100.0% | 0 | 0.0% | 2700 | 100.0% |
| Percent Central * Trial Number | 2700 | 100.0% | 0 | 0.0% | 2700 | 100.0% |
| Mean Low * Trial Number | 2700 | 100.0% | 0 | 0.0% | 2700 | 100.0% |
| Sum Low * Trial Number | 2700 | 100.0% | 0 | 0.0% | 2700 | 100.0% |
| Percent Low * Trial Number | 2700 | 100.0% | 0 | 0.0% | 2700 | 100.0% |

TABLE 3

Trial Data Report: High/Central Data

| Trial Number |  | Mean High | Sum High | Percent High | Mean Central | Sum Central |
|---|---|---|---|---|---|---|
| 0 | Mean | 60441.40882 | 3463285.52533 | 2.49365 | 1431.29627 | 3667946.48301 |
|  | N | 680 | 680 | 680 | 680 | 680 |
| 1 | Mean | 62266.64153 | 3566981.89677 | 2.44943 | 1458.36740 | 3801798.48116 |
|  | N | 680 | 680 | 680 | 680 | 680 |
| 2 | Mean | 63362.45393 | 3652145.44374 | 2.42731 | 1480.47843 | 3905928.50434 |
|  | N | 680 | 680 | 680 | 680 | 680 |
| 3 | Mean | 63669.41972 | 3640721.49817 | 2.40858 | 1476.96149 | 3898443.44132 |
|  | N | 660 | 660 | 660 | 660 | 660 |
| Total | Mean | 62425.83701 | 3580339.60650 | 2.44501 | 1461.66341 | 3817937.27032 |
|  | N | 2700 | 2700 | 2700 | 2700 | 2700 |

TABLE 4

Trial Data Report: Low/Central Data

| Trial Number | | Percent Central | Mean Low | Sum Low | Percent Low |
|---|---|---|---|---|---|
| 0 | Mean | 95.02779 | −60503.43859 | −3452105.32662 | 2.47857 |
|   | N | 680 | 680 | 680 | 680 |
| 1 | Mean | 95.11484 | −62346.94574 | −3557907.97965 | 2.43574 |
|   | N | 680 | 680 | 680 | 680 |
| 2 | Mean | 95.15857 | −63459.10523 | −3643660.27349 | 2.41412 |
|   | N | 680 | 680 | 680 | 680 |
| 3 | Mean | 95.19592 | −63776.65443 | −3632811.58076 | 2.39551 |
|   | N | 660 | 660 | 660 | 660 |
| Total | Mean | 95.12375 | −62512.23882 | −3571168.02872 | 2.43125 |
|   | N | 2700 | 2700 | 2700 | 2700 |

TABLE 5

ANOVA Analysis

| | | Sum of Squares | df | Mean Square | F | Sig. |
|---|---|---|---|---|---|---|
| Mean High | Between Groups | 4312262444.751 | 3 | 1437420814.917 | 13.645 | .000 |
| | Within Groups | 284012703678.591 | 2696 | 105345958.338 | | |
| | Total | 288324966123.341 | 2699 | | | |
| Sum High | Between Groups | 15350933996793.432 | 3 | 5116977998931.144 | 1.802 | .145 |
| | Within Groups | 7655672590919036.000 | 2696 | 2839641168738.515 | | |
| | Total | 7671023524915829.000 | 2699 | | | |
| Percent High | Between Groups | 2.711 | 3 | .904 | 1.085 | .354 |
| | Within Groups | 2244.581 | 2696 | .833 | | |
| | Total | 2247.291 | 2699 | | | |
| Mean Central | Between Groups | 1029642.012 | 3 | 343214.004 | 4.398 | .004 |
| | Within Groups | 210405431.276 | 2696 | 78043.558 | | |
| | Total | 211435073.288 | 2699 | | | |
| Sum Central | Between Groups | 25017725514960.570 | 3 | 8339241838320.190 | 2.093 | .099 |
| | Within Groups | 10739437870824010.000 | 2696 | 3983471020335.315 | | |
| | Total | 10764455596338970.000 | 2699 | | | |
| Percent Central | Between Groups | 10.578 | 3 | 3.526 | 1.069 | .361 |
| | Within Groups | 8895.687 | 2696 | 3.300 | | |
| | Total | 8906.265 | 2699 | | | |
| Mean Low | Between Groups | 4427399097.421 | 3 | 1475799699.140 | 13.855 | .000 |
| | Within Groups | 287178965947.528 | 2696 | 106520387.963 | | |
| | Total | 291606365044.949 | 2699 | | | |
| Sum Low | Between Groups | 15840631564575.242 | 3 | 5280210521525.081 | 1.850 | .136 |
| | Within Groups | 7693750519184988.000 | 2696 | 2853765029371.286 | | |
| | Total | 7709591150749563.000 | 2699 | | | |
| Percent Low | Between Groups | 2.579 | 3 | .860 | 1.052 | .368 |
| | Within Groups | 2203.661 | 2696 | .817 | | |
| | Total | 2206.240 | 2699 | | | |

TABLE 6

Post Hoc Multiple Comparison

| Dependent Variable | (I) Trial Number | (J) Trial Number | Mean Difference (I−J) | Std. Error | Sig. | 95% Confidence Interval Lower Bound | 95% Confidence Interval Upper Bound |
|---|---|---|---|---|---|---|---|
| Mean High | 0 | 1 | −1825.232710• | 556.633680 | .013 | −3382.27673 | −268.18869 |
| | | 2 | −2921.045109• | 556.633680 | .000 | −4478.08912 | −1364.00109 |
| | | 3 | −3228.010901• | 560.834749 | .000 | −4796.80636 | −1659.21544 |
| | 1 | 0 | 1825.232710• | 556.633680 | .013 | 268.18869 | 3382.27673 |
| | | 2 | −1095.812399 | 556.633680 | .275 | −2652.85641 | 461.23162 |
| | | 3 | −1402.778190 | 560.834749 | .100 | −2971.57365 | 166.01727 |

TABLE 6-continued

Post Hoc Multiple Comparison

| Dependent Variable | (I) Trial Number | (J) Trial Number | Mean Difference (I-J) | Std. Error | Sig. | 95% Confidence Interval Lower Bound | Upper Bound |
|---|---|---|---|---|---|---|---|
| | 2 | 0 | 2921.045109• | 556.633680 | .000 | 1364.00109 | 4478.08912 |
| | | 1 | 1095.812399 | 556.633680 | .275 | −461.23162 | 2652.85641 |
| | | 3 | −306.965792 | 560.834749 | .960 | −1875.76125 | 1261.82967 |
| | 3 | 0 | 3228.010901• | 560.834749 | .000 | 1659.21544 | 4796.80636 |
| | | 1 | 1402.778190 | 560.834749 | .100 | −166.01727 | 2971.57365 |
| | | 2 | 306.965792 | 560.834749 | .960 | −1261.82967 | 1875.76125 |
| Sum High | 0 | 1 | −103696.371441 | 91388.652416 | .732 | 359333.35386 | 151940.61097 |
| | | 2 | −188859.918413 | 91388.652416 | .234 | 444496.90083 | 66777.06400 |
| | | 3 | −177435.972842 | 92078.387880 | .294 | 435002.31834 | 80130.37266 |
| | 1 | 0 | 103696.371441 | 91388.652416 | .732 | 151940.61097 | 359333.35386 |
| | | 2 | −85163.546972 | 91388.652416 | .833 | 340800.52939 | 170473.43544 |
| | | 3 | −73739.601401 | 92078.387880 | .887 | 331305.94690 | 183826.74410 |
| | 2 | 0 | 188859.918413 | 91388.652416 | .234 | −66777.06400 | 444496.90083 |
| | | 1 | 85163.546972 | 91388.652416 | .833 | −170473.43544 | 340800.52939 |
| | | 3 | 11423.945572 | 92078.387880 | .999 | −246142.39993 | 268990.29107 |
| | 3 | 0 | 177435.972842 | 92078.387880 | .294 | −80130.37266 | 435002.31834 |
| | | 1 | 73739.601401 | 92078.387880 | .887 | −183826.74410 | 331305.94690 |
| | | 2 | −11423.945572 | 92078.387880 | .999 | −268990.29107 | 246142.39993 |
| Percent High | 0 | 1 | .044213 | .049484 | .850 | −.09421 | .18263 |
| | | 2 | .066334 | .049484 | .616 | −.07209 | .20475 |
| | | 3 | .085064 | .049858 | .406 | −.05440 | .22453 |
| | 1 | 0 | −.044213 | .049484 | .850 | −.18263 | .09421 |
| | | 2 | .022121 | .049484 | .978 | −.11630 | .16054 |
| | | 3 | .040850 | .049858 | .880 | −.09861 | .18032 |
| | 2 | 0 | −.066334 | .049484 | .616 | −.20475 | .07209 |
| | | 1 | −.022121 | .049484 | .978 | −.16054 | .11630 |
| | | 3 | .018730 | .049858 | .986 | −.12074 | .15819 |
| | 3 | 0 | −.085064 | .049858 | .406 | −.22453 | .05440 |
| | | 1 | −.040850 | .049858 | .880 | −.18032 | .09861 |
| | | 2 | −.018730 | .049858 | .986 | −.15819 | .12074 |
| Mean Central | 0 | 1 | −27.071124 | 15.150573 | .363 | −69.45108 | 15.30883 |
| | | 2 | −49.182151 | 15.150573 | .015 | −91.56211 | −6.80220 |
| | | 3 | −45.665216 | 15.264919 | .030 | −88.36502 | −2.96541 |
| | 1 | 0 | 27.071124 | 15.150573 | .363 | −15.30883 | 69.45108 |
| | | 2 | −22.111028 | 15.150573 | .546 | −64.49098 | 20.26893 |
| | | 3 | −18.594092 | 15.264919 | .686 | −61.29390 | 24.10571 |
| | 2 | 0 | 49.182151 | 15.150573 | .015 | 6.80220 | 91.56211 |
| | | 1 | 22.111028 | 15.150573 | .546 | −20.26893 | 64.49098 |
| | | 3 | 3.516936 | 15.264919 | .997 | −39.18287 | 46.21674 |
| | 3 | 0 | 45.665216 | 15.264919 | .030 | 2.96541 | 88.36502 |
| | | 1 | 18.594092 | 15.264919 | .686 | −24.10571 | 61.29390 |
| | | 2 | −3.516936 | 15.264919 | .997 | −46.21674 | 39.18287 |
| Sum Central | 0 | 1 | −133851.998154 | 108240.894473 | .676 | −436628.92839 | 168924.93208 |
| | | 2 | −237982.021328 | 108240.894473 | .185 | 540758.95156 | 64794.90891 |
| | | 3 | −230496.958314 | 109057.818473 | .216 | −535559.02988 | 74565.11325 |
| | 1 | 0 | 133851.998154 | 108240.894473 | .676 | −168924.93208 | 436628.92839 |
| | | 2 | −104130.023174 | 108240.894473 | .819 | −406906.95341 | 198646.90706 |
| | | 3 | −96644.960159 | 109057.818473 | .853 | −401707.03172 | 208417.11140 |
| | 2 | 0 | 237982.021328 | 108240.894473 | .185 | −64794.90891 | 540758.95156 |
| | | 1 | 104130.023174 | 108240.894473 | .819 | −198646.90706 | 406906.95341 |
| | | 3 | 7485.063014 | 109057.818473 | 1.000 | −297577.00855 | 312547.13458 |
| | 3 | 0 | 230496.958314 | 109057.818473 | .216 | −74565.11325 | 535559.02988 |
| | | 1 | 96644.960159 | 109057.818473 | .853 | −208417.11140 | 401707.03172 |
| | | 2 | −7485.063014 | 109057.818473 | 1.000 | −312547.13458 | 297577.00855 |
| Percent Central | 0 | 1 | −.087053 | .098512 | .854 | −.36262 | .18851 |
| | | 2 | −.130781 | .098512 | .623 | −.40634 | .14478 |
| | | 3 | −.168131 | .099256 | .412 | −.44577 | .10951 |
| | 1 | 0 | .087053 | .098512 | .854 | −.18851 | .36262 |
| | | 2 | −.043728 | .098512 | .978 | −.31929 | .23184 |
| | | 3 | −.081079 | .099256 | .881 | −.35872 | .19656 |
| | 2 | 0 | .130781 | .098512 | .623 | −.14478 | .40634 |
| | | 1 | .043728 | .098512 | .978 | −.23184 | .31929 |
| | | 3 | −.037351 | .099256 | .986 | −.31499 | .24029 |
| | 3 | 0 | .168131 | .099256 | .412 | −.10951 | .44577 |
| | | 1 | .081079 | .099256 | .881 | −.19656 | .35872 |
| | | 2 | .037351 | .099256 | .986 | −.24029 | .31499 |
| Mean Low | 0 | 1 | 1843.507144• | 559.727843 | .013 | 277.80798 | 3409.20631 |
| | | 2 | 2955.666640• | 559.727843 | .000 | 1389.96747 | 4521.36581 |
| | | 3 | 3273.215836• | 563.952264 | .000 | 1695.69990 | 4850.73177 |
| | 1 | 0 | −1843.507144• | 559.727843 | .013 | −3409.20631 | −277.80798 |
| | | 2 | 1112.159496 | 559.727843 | .267 | −453.53967 | 2677.85866 |
| | | 3 | 1429.708692 | 563.952264 | .093 | −147.80724 | 3007.22462 |

TABLE 6-continued

Post Hoc Multiple Comparison

| Dependent Variable | (I) Trial Number | (J) Trial Number | Mean Difference (I-J) | Std. Error | Sig. | 95% Confidence Interval Lower Bound | 95% Confidence Interval Upper Bound |
|---|---|---|---|---|---|---|---|
| | 2 | 0 | −2955.666640• | 559.727843 | .000 | −4521.36581 | −1389.96747 |
| | | 1 | −1112.159496 | 559.727843 | .267 | −2677.85866 | 453.53967 |
| | | 3 | 317.549196 | 563.952264 | .957 | −1259.96673 | 1895.06513 |
| | 3 | 0 | −3273.215836• | 563.952264 | .000 | −4850.73177 | −1695.69990 |
| | | 1 | −1429.708692 | 563.952264 | .093 | −3007.22462 | 147.80724 |
| | | 2 | −317.549196 | 563.952264 | .957 | −1895.06513 | 1259.96673 |
| Sum Low | 0 | 1 | 105802.653024 | 91615.645809 | .721 | −150469.28684 | 362074.59289 |
| | | 2 | 191554.946868 | 91615.645809 | .224 | −64716.99300 | 447826.88674 |
| | | 3 | 180706.254139 | 92307.094454 | .280 | −77499.84102 | 438912.34929 |
| | 1 | 0 | −105802.653024 | 91615.645809 | .721 | −362074.59289 | 150469.28684 |
| | | 2 | 85752.293844 | 91615.645809 | .831 | −170519.64602 | 342024.23371 |
| | | 3 | 74903.601115 | 92307.094454 | .883 | 183302.49404 | 333109.69627 |
| | 2 | 0 | −191554.946868 | 91615.645809 | .224 | −447826.88674 | 64716.99300 |
| | | 1 | −85752.29384 | 91615.645809 | .831 | −342024.23371 | 170519.64602 |
| | | 3 | −10848.692729 | 92307.094454 | 1.000 | −269054.78788 | 247357.40243 |
| | 3 | 0 | −180706.254139 | 92307.094454 | .280 | −438912.34929 | 77499.84102 |
| | | 1 | −74903.601115 | 92307.09445 | .883 | −333109.69627 | 183302.49404 |
| | | 2 | 10848.692729 | 92307.094454 | 1.000 | −247357.40243 | 269054.78788 |
| Percent Low | 0 | 1 | .042825 | .049031 | .858 | −.09433 | .17998 |
| | | 2 | .064451 | .049031 | .631 | −.07270 | .20160 |
| | | 3 | .083062 | .049401 | .419 | −.05513 | .22125 |
| | 1 | 0 | −.042825 | .049031 | .858 | −.17998 | .09433 |
| | | 2 | .021626 | .049031 | .978 | −.11553 | .15878 |
| | | 3 | .040237 | .049401 | .882 | −.09795 | .17842 |
| | 2 | 0 | −.064451 | .049031 | .631 | −.20160 | .07270 |
| | | 1 | −.021626 | .049031 | .978 | −.15878 | .11553 |
| | | 3 | .018610 | .049401 | .986 | −.11958 | .15680 |
| | 3 | 0 | −.083062 | .049401 | .419 | −.22125 | .05513 |
| | | 1 | −.040237 | .049401 | .882 | −.17842 | .09795 |
| | | 2 | −.018610 | .049401 | .986 | −.15680 | .11958 |

To provide further context for the comparative results, means for groups in homogeneous subsets are also provided in Tables 7-15, below. This data uses a Harmonic Mean Sample Size=674.887. (Note: The group sizes are unequal. The harmonic mean of the group sizes is used. Type I error levels are not guaranteed.)

TABLE 7

Mean High

| Trial Number | N | Subset for alpha = 0.05 1 | Subset for alpha = 0.05 2 |
|---|---|---|---|
| 0 | 680 | 60441.40882 | |
| 1 | 680 | | 62266.64153 |
| 2 | 680 | | 63362.45393 |
| 3 | 660 | | 63669.41972 |
| Sig. | | 1.000 | .098 |

TABLE 8

Sum High

| Trial Number | N | Subset for alpha = 0.05 1 |
|---|---|---|
| 0 | 680 | 3463285.52533 |
| 1 | 680 | 3566981.89677 |
| 3 | 660 | 3640721.49817 |
| 2 | 680 | 3652145.44374 |
| Sig. | | .237 |

TABLE 9

Percent High

| Trial Number | N | Subset for alpha = 0.05 1 |
|---|---|---|
| 3 | 660 | 2.40858 |
| 2 | 680 | 2.42731 |
| 1 | 680 | 2.44943 |
| 0 | 680 | 2.49365 |
| Sig. | | .402 |

TABLE 10

Mean Central

| Trial Number | N | Subset for alpha = 0.05 1 | Subset for alpha = 0.05 2 |
|---|---|---|---|
| 0 | 680 | 1431.29627 | |
| 1 | 680 | 1458.36740 | 1458.36740 |
| 3 | 660 | | 1476.96149 |
| 2 | 680 | | 1480.47842 |
| Sig. | | .367 | .549 |

TABLE 11

Sum Central

| Trial Number | N | Subset for alpha = 0.05 1 |
|---|---|---|
| 0 | 680 | 3667946.48301 |
| 1 | 680 | 3801798.48116 |

TABLE 11-continued

Sum Central

| Trial Number | N | Subset for alpha = 0.05<br>1 |
|---|---|---|
| 3 | 660 | 3898443.44132 |
| 2 | 680 | 3905928.50434 |
| Sig. | | .187 |

TABLE 12

Percent Central

| Trial Number | N | Subset for alpha = 0.05<br>1 |
|---|---|---|
| 0 | 680 | 95.02779 |
| 1 | 680 | 95.11484 |
| 2 | 680 | 95.15857 |
| 3 | 660 | 95.19592 |
| Sig. | | .409 |

TABLE 13

Mean Low

| Trial Number | N | Subset for alpha = 0.05 | |
|---|---|---|---|
| | | 1 | 2 |
| 3 | 660 | −63776.65443 | |
| 2 | 680 | −63459.10523 | |
| 1 | 680 | −62346.94574 | |
| 0 | 680 | | −60503.43859 |
| Sig. | | .091 | 1.000 |

TABLE 14

Sum Low

| Trial Number | N | Subset for alpha = 0.05<br>1 |
|---|---|---|
| 2 | 680 | −3643660.27349 |
| 3 | 660 | −3632811.58076 |
| 1 | 680 | −3557907.97965 |
| 0 | 680 | −3452105.32663 |
| Sig. | | .227 |

TABLE 15

Percent Low

| Trial Number | N | Subset for alpha = 0.05<br>1 |
|---|---|---|
| 3 | 660 | 2.39551 |
| 2 | 680 | 2.41412 |
| 1 | 680 | 2.43574 |

TABLE 15-continued

Percent Low

| Trial Number | N | Subset for alpha = 0.05<br>1 |
|---|---|---|
| 0 | 680 | 2.47857 |
| Sig. | | .416 |

Conclusion: This exemplary embodiment demonstrates how a system is able to analyze how user intention can entrain randomly-generated signals, which can be analyzed.

Example 2: Study of Device Sensitivity to Entrainment Using Mechanical Manipulator Methodology: In another exemplary study, fifty-nine (59) adult subjects participated in a research project using a device as described in reference to FIGS. 1-6. This research project subjected the research subjects to two intend trials and two non-intend trials. The first non-intend trial placed the research subjects in an empty room. A 5-minute delay in data capture was set, and then 5 minutes of unprocessed frequency data was digitally saved. Following the first non-intend trial, each research subject subjected to a first intend trial, where the research subjects were tasked with stacking foam blocks with a mechanical hand controlled through an interface device according to embodiments. A second non-intend trial was accomplished as described above. After the second non-intend trial, each research subject performed a second intend trial, where the research subjects were tasked with stacking and restacking the foam blocks as smoothly and rhythmically as possible, using the research subjects' perceived and most successful mental strategies. Data captured from the two non-intend trials were stored in association with the two intend trials.

Data Analysis: The two trials captured non-intend and intend data, which were stored in association with each other. The trended signal output of the MMIP was input to a hardware counter digitizer and output as discrete digitized frequencies. The discrete digitized frequencies were input to a computer for software processing. Software processing included proportional normalization of frequencies, rise and fall trending of normalized proportional frequencies, and frequency spectral analysis. Both characteristics of signal trend and frequency spectrum have been used to drive the mechanical hand. The wave form type movement of the mechanical hand was data captured and processed to determine various characteristics of the wave forms including adjacent proportional percent of similarity and number of those wave forms that met or exceeded set parameters, (>=75% for example). Indexing was used to parse wave forms with determined features and process the parsed signal (rise and fall trend for example) to determine various characteristics including rate of change, frequency shift and frequency density as examples. The data from these trials is provided in Tables 1-15, below.

Results: Two non-intend and two intend 5-minute trials for each of 59 adult participants were analyzed. The parsed rise and fall trending signal's 2nd derivative bias, analyzed using an ANOVA, was not statistically significant when comparing non-intend trial 1 with non-intend trial 2 and non-intend trial 1 with intend trial 1. Non-intend trial 2 and intend trial 2 were statistically significantly different at a p=0.029. The % difference in the non-intend mean of −0.38953 and intend mean of 0.57959 equaled an absolute difference of 32.79%.

TABLE 16

Descriptives

|  |  | N | Mean | Std. Deviation | Std. Error | 95% Confidence Interval for Mean | | Minimum | Maximum |
| --- | --- | --- | --- | --- | --- | --- | --- | --- | --- |
|  |  |  |  |  |  | Lower Bound | Upper Bound |  |  |
| Derivative Bias |  |  |  |  |  |  |  |  |  |
| 0 = non-intend | 0 | 59 | −.38953 | 2.660181 | .346326 | −1.08277 | .30372 | −6.510 | 6.273 |
| 1 = intend | 1 | 59 | .57959 | 2.062787 | .268552 | .04203 | 1.11716 | −4.045 | 5.359 |
|  | Total | 118 | .09503 | 2.419546 | .222737 | −.34609 | .53615 | −6.510 | 6.273 |

TABLE 17

ANOVA

|  |  | Sum of Squares | df | Mean Square | F | Sig. |
| --- | --- | --- | --- | --- | --- | --- |
| Derivative Bias | Between Groups | 27.706 | 1 | 27.706 | 4.890 | 0.029 |
|  | Within Groups | 657.236 | 116 | 5.666 |  |  |
|  | Total | 684.942 | 117 |  |  |  |

Conclusion: This exemplary embodiment demonstrates how analysis of an entrained signal can be used to control a mechanical device to accomplish a task.

Example 3: Study of Device Sensitivity to Entrainment Using Mechanical Manipulator and Frequency Processing Methodology: In another embodiment, a 10-second rise and fall trend running-FFT (fast Fourier transform) of each 5 minute (2 each) intend and non-intend trials was organized into a 20-bin percent-histogram of spectral power for 48 of the 59 adult participants discussed above in Example 2.

Data Analysis: An ANOVA between intend and non-intend trials was performed on an intend N=387,791 and a non-intend N=390,567.

Results: There was a statistically significant difference between the intend and non-intend 2nd trials for the histogram bin associated with 3.75 Hz with a non-intend mean of 1.85649% and intend mean of 1.86664%, an F of 23.667 and p=0.000, and the histogram bin associated with 4.00 Hz. with a non-intend mean of 1.71451% and intend mean of 1.72700%, an F of 40.270 and p=0.000.

Conclusion: This exemplary embodiment demonstrates that user intention has a statistically-significant and measurable impact on certain wavelengths.

Example 4: Effects of an Infrared Brain Stimulation Device on the Enhancement of Mental Intention as Reflected by the Present Mind-Machine Interface Device's Performance Metric Methodology: A pilot study was initiated for one subject to test a potential wave form identification strategy and performance metric for the present Mind-Machine Interface Device. Two 5-minute non-intend and three intend trials where performed with the third intend trial occurring after the use of an infrared brain stimulation device (Maculume LTD Cerebrolite, a prototype) whose purpose was to improve mental intention performance. The rise and fall trend of the proportional frequency sum of 1000 data values was transformed, to selected FFT spectral frequency ranges, in post processing, as the output used to control the mechanical hand. Further, the rise and fall trend of the proportional frequency sum of 1000 data values was transformed, to a running average as an output used to control the mechanical hand. The wave forms manifested by these processes where selected temporally if they were greater than or equal to 2 seconds and less than or equal to 6 seconds. This corresponds to the controlling time frame for the participant to move blocks from one location to another. Further, each wave form was selected if greater than or equal to 60% proportional to its adjacent wave form in iteration for all wave forms in the data set.

Data Analysis: The $2^{nd}$ derivative bias of rise and fall trend of the proportional frequency sum of 1000 data values for each rising component of the wave form's period was calculated. The $2^{nd}$ derivative bias sum and average of all qualifying wave forms was calculated and the trials compared as percent differences.

Results: The wave forms for each trial were, for the most part, consistent in number with some differences that cannot be yet accounted for. Both the sums and averages of the 2nd derivative bias were consistent in the proportional differences between intend trials 1 to 3 as compared to non-intend trial 2. Noteworthy is the over 300% difference between the post-infrared brain stimulation intend trial #3 and the non-intend trial #2.

TABLE 18

Trial Data Report

|  | Intend Trial 1 | Intend Trial 2 | Intend trial 3 post IR | Non Intend Trial 1 | Non Intend Trial 2 |
|---|---|---|---|---|---|
| Sum of Derivative Bias | 11.324 | 9.199 | 17.244 | −16.578 | 5.089 |
| % Difference Intend Trials 1-3 to Non-intend Trial 1 | 222.5192% | 180.7624% | 338.8485% | | |
| Average Derivative Bias | 0.205891 | 0.262829 | 0.453789 | −0.40434 | 0.154212 |
| % Difference Intend Trials 1-3 to Non-intend Trial 2 | 213.3515% | 190.4594% | 294.2630% | | |

TABLE 19

Rise Fall Trend all mean stats

|  | Intend Trial 1 | Intend Trial 2 | Intend Trial 3 | Non-Intend Trial 1 | Non-Intend Trial 2 |
|---|---|---|---|---|---|
| Total Wave Forms | 113 | 102 | 108 | 106 | 86 |
| Waves that did not make the criteria | 41 | 49 | 52 | 47 | 35 |
| Waves that made the criteria | 72 | 53 | 56 | 59 | 51 |

TABLE 20

Rise Fall Trend all FFT stats

|  | Intend Trial 1 | Intend Trial 2 | Intend Trial 3 | Non-Intend Trial 1 | Non-Intend Trial 2 |
|---|---|---|---|---|---|
| Total Wave Forms | 84 | 92 | 96 | 92 | 106 |
| Waves that did not make the criteria | 44 | 40 | 45 | 50 | 38 |
| Waves that made the criteria | 40 | 52 | 51 | 42 | 68 |

The strategy used to identify intend VS non-intend characteristics appears to be robust as a performance metric. Several qualifying techniques were used to establish this level of percent difference including:

Only the rise (hand closing) wave form period was used.
Only adjacent wave form proportional percentages greater than or equal to 60% where used.
Only wave forms that occurred in 2 to 6 seconds where used. Interesting to note is that the average wave form time was approximately 3.5 seconds.
The $2^{nd}$ derivative bias of the rising portion of the qualified wave forms appears to be robust and discriminating with all intend trials different in percentage from non-intend trials by at least 180% and most significant is the percent difference of the post-infrared brain stimulation trial of as much as 338% difference Conclusion: This exemplary embodiment demonstrates that IR stimulation can improve mental intention performance.

DOCTRINE OF EQUIVALENTS

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. An external intentionality interface apparatus comprising:
a plurality of sub-atomic-based random signal sources capable of being entrained by an external intentionality;
a coupling circuit in signal communication with the plurality of sub-atomic-based random signal sources, configured to combine the randomly-generated signals from said plurality of sub-atomic-based signal sources into a single coupled signal capable of increased order with the entrainment of the external intentionality;
a signal amplifier in signal communication with the coupling circuit to amplify the single coupled signal;
a dynamic bias circuit to maintain a mean-centered bias of the single coupled signal;
a signal voltage trend indicator in signal communication with the signal amplifier and configured to detect the voltage difference between a non-delayed signal and a propagation-delayed signal and to produce a logic trend output signal indicative of the voltage difference, where the digitally-processed trend output signal is provided as a first logic state where the trend is toward a negative voltage and a second logic state where the trend is toward a positive voltage, and wherein the logic trend output signal from the signal voltage trend indicator is a rising or falling logic state;
a period-clock counting and digitizing apparatus, wherein the period-clock counting apparatus clocks and digitizes the rising or falling logic states of the output signal to produce a continuous consecutive signal of discrete digitized clock count data values that are then outputted as a plurality of discrete packets; and
a processor configured to operate on the discrete packets of digitized clock count data values to output at least one entrainment metric control signal wherein at least one entrainment metric control signal provides an indication of the presence of the external intentionality entrained within the single coupled signal wherein each intention-entrained signal exceeding a predetermined entrainment metric threshold is a qualified event.

2. The apparatus of claim 1, wherein the plurality of sub-atomic-based random signal sources comprise reverse-biased Zener diodes configured to produce multiple random signals at their respective breakdown voltage knees.

3. The apparatus of claim 2, wherein the sub-atomic-based random signal sources comprise at least two Zener diodes.

4. The apparatus of claim 1, wherein the signal voltage trend indicator comprises a modulatable laser photonic source.

5. The apparatus of claim 4, further comprising a photonic crystal waveguide interferometer configured to detect a greater phase state coherence and convert this phase state into a variable electrical signal.

6. The apparatus of claim 1, wherein the plurality of randomly-generated signals are capacitively coupled.

7. The apparatus of claim 1, wherein the dynamic bias circuit is analog.

8. The apparatus of claim 1, wherein the processor performs a derivative calculation on the discrete packets of digitized clock count data values output from the period clock-counting and digitizing apparatus to output the at least one entrainment metric control signal.

9. The apparatus of claim 1,
wherein the output signal from the signal voltage trend indicator is output as a series of packets of discrete digitized frequency data,
wherein the period-clock counting apparatus normalizes the digitized frequency data as proportional values between adjacent digitized frequency values within each packet,
wherein the coherence score is generated by summing the normalized digitized frequency data within each packet,
wherein the trend of the series of packets is determined by determining changes in the coherence score between each packet in the series of packets,
wherein the frequency components of the trend are identified by running by a frequency sorting algorithm discriminating the greatest percent of frequency distribution density values, and
outputs the greatest percent frequency distribution density values as a controlling signal.

10. The apparatus of claim 1, wherein the presence of a qualified event in the output coupled signal is utilized as a control signal for a device in signal communication therewith.

11. The apparatus of claim 1, further comprising a circuit feedback loop, wherein the circuit feedback loop is configured to:
determine at least one of the amount of qualified events and the temporal density of qualified events; and
automatically adjust the DC bias of the single coupled signal generated from the coupled randomly-generated signals to regulate the mean voltage bias, wherein direction of regulatory bias is predetermined by goal-directed entrainment metric thresholds.

12. The apparatus of claim 1, further comprising a plurality of nodes of multiple randomly-generated signals disposed in proximity to each other node and configured to entrain each other node such that the nodes act collectively to accomplish a programmed directive, via goal directed programming and feedback control processing.

13. A method for entraining from user intentionality of randomly-generated signals to generate a single control signal for controlling an external device comprising:
providing an external intentionality interface apparatus to the user, wherein the interface apparatus comprises:
a plurality of sub-atomic-based random signal sources capable of being entrained by an external intentionality,
a coupling circuit in signal communication with the plurality of sub-atomic-based random signal sources, configured to combine the randomly-generated signals from said plurality of sub-atomic-based signal sources into a single coupled signal capable of increased order with the entrainment of the external intentionality,
a signal amplifier in signal communication with the coupling circuit to amplify the single coupled signal,
a dynamic bias circuit to maintain a means-centered bias of the coupled randomly-generated signal;
a signal voltage trend indicator in signal communication with the signal amplifier and configured to detect the voltage difference between a non-delayed signal and a propagation-delayed signal and to produce a logic trend output signal indicative of the voltage difference, where the digitally-processed trend output signal is provided as a first logic state where the trend is toward a negative voltage and a second logic state where the trend is toward a positive voltage, and wherein the logic trend output signal from the signal voltage trend indicator is a rising or falling logic state,
a period-clock counting and digitizing apparatus, wherein the period-clock counting apparatus clocks and digitizes the rising or falling logic states of the output signal to produce a continuous consecutive signal of discrete digitized clock count data values that are then outputted as a plurality of discrete packets, and
a processor configured to operate on the discrete packets of digitized clock count data values to output at least one entrainment metric control signal wherein at least one entrainment metric control signal provides an indication of the presence of the external intentionality entrained within the single coupled signal wherein each intention-entrained signal exceeding a predetermined entrainment metric threshold is a qualified event; and
directing the user to make an intentional change to a state of an observable stimulus configured to be representative of the logic trend output signal.

14. The method of claim 13, further comprising:
processing the intentional change as a qualified event; and
generating a control signal from the qualified event.

15. The method of claim 14, wherein the control signal directs the operation of an external device in signal communication with the mind-machine interface apparatus.

16. The method of claim 13, wherein the mind-machine interface apparatus further comprises an external device in signal communication with the mind-machine interface apparatus.

17. The method of claim 13, wherein the plurality of sub-atomic-based random signal sources comprise reverse-biased Zener diodes configured to produce multiple random signals at their respective breakdown voltage knees.

18. The method of claim 17, wherein the sub-atomic-based random signal sources comprise at least two Zener diodes.

19. The method of claim 13, wherein the signal voltage trend indicator comprises a modulatable laser photonic source.

20. The method of claim 13, wherein the plurality of randomly-generated signals are capacitively coupled.

21. The method of claim 13, wherein the processor performs a derivative calculation on the discrete packets of digitized clock count data values output from the period clock-counting and digitizing apparatus to output the at least one entrainment metric control signal.

22. The method of claim 13, wherein the output signal from the signal voltage trend indicator is output as a series of packets of discrete digitized frequency data, and wherein the period-clock counting apparatus:
- normalizes the digitized frequency data as proportional values between adjacent digitized frequency values within each packet;
- wherein the coherence score is generated by summing the normalized digitized frequency data within each packet;
- wherein the trend of the series of packets is determined by determining changes in the coherence score between each packet in the series of packets;
- wherein the frequency components of the trend are identified by running a frequency sorting algorithm discriminating the greatest percent of frequency distribution density values; and
- outputs the greatest percent frequency distribution density values as a controlling signal.

\* \* \* \* \*